(12) United States Patent
Hamamoto et al.

(10) Patent No.: US 9,808,379 B2
(45) Date of Patent: Nov. 7, 2017

(54) PANTS-TYPE WEARING ARTICLE AND PRODUCTION METHOD FOR SAME

(71) Applicant: KAO CORPORATION, Tokyo (JP)

(72) Inventors: Shinji Hamamoto, Shimotsuke (JP); Koji Imai, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 62 days.

(21) Appl. No.: 15/033,280

(22) PCT Filed: Oct. 24, 2014

(86) PCT No.: PCT/JP2014/078296
§ 371 (c)(1),
(2) Date: Apr. 29, 2016

(87) PCT Pub. No.: WO2015/064486
PCT Pub. Date: May 7, 2015

(65) Prior Publication Data
US 2016/0250082 A1 Sep. 1, 2016

(30) Foreign Application Priority Data
Nov. 1, 2013 (JP) .................................. 2013-228015

(51) Int. Cl.
*A61F 13/496* (2006.01)
*B29C 65/16* (2006.01)
(Continued)

(52) U.S. Cl.
CPC .......... *A61F 13/49007* (2013.01); *A41B 9/00* (2013.01); *A61F 13/15739* (2013.01);
(Continued)

(58) Field of Classification Search
CPC .......... A61F 13/15739; A61F 13/49007; A61F 13/496; A61F 13/4963; A61F 13/51401;
(Continued)

(56) References Cited

U.S. PATENT DOCUMENTS 3,449,196 A * 6/1969 Hashimoto ............. B31B 70/00
156/498
4,115,683 A 9/1978 Clark et al.
(Continued)

FOREIGN PATENT DOCUMENTS

CN 1243691 A 2/2000
CN 1956836 A 5/2007
(Continued)

OTHER PUBLICATIONS

Extended European Search Report dated May 12, 2017, for corresponding European Application No. 14859032.6.
(Continued)

*Primary Examiner* — Kathryn E Ditmer
(74) *Attorney, Agent, or Firm* — Birch, Stewart, Kolasch & Birch, LLP

(57) ABSTRACT

A pull-on garment (1) includes an outer cover (3) forming an outer surface of the garment, both lateral side edge portions of the outer cover in a front body portion F and both lateral side edge portions of the outer cover in a back body portion R being joined to each other to form a pair of side seals (4), a waist opening (8), and a pair of leg openings (9). Each of the side seals (4) includes a seal edge portion (41) where the edge portion (3F) of the outer cover (3) in the front body portion F and the edge portion of the outer cover (3) in the back body portion R are bonded to each other by a continuous linear fusion-bonded portion (40) extending in a longitudinal direction of the side seal (4). In a cross-section orthogonal to a direction in which the side seal (4) extends, the fusion-bonded portion (40) includes a narrow section (4F) which is formed at a middle portion thereof in the thickness direction Q and of which a width W along the inner-to-outer direction P is small. The narrow section (4F) includes broad sections (4A, 4B) which are provided on both sides of the narrow section (4F) in the thickness direction Q (Continued)

and of which the width W is larger than the width of the narrow section (4F).

15 Claims, 8 Drawing Sheets

(51) Int. Cl.

| | |
|---|---|
| *B29C 65/74* | (2006.01) |
| *A41B 9/00* | (2006.01) |
| *A61F 13/49* | (2006.01) |
| *A61F 13/15* | (2006.01) |
| *B29C 65/00* | (2006.01) |
| *A61F 13/514* | (2006.01) |
| *B29L 31/48* | (2006.01) |

(52) U.S. Cl.
CPC .... *A61F 13/49011* (2013.01); *A61F 13/4963* (2013.01); *A61F 13/51401* (2013.01); *B29C 65/1648* (2013.01); *B29C 65/1654* (2013.01); *B29C 65/1696* (2013.01); *B29C 65/7473* (2013.01); *B29C 66/1122* (2013.01); *B29C 66/431* (2013.01); *B29C 66/723* (2013.01); *B29C 66/72941* (2013.01); *B29C 66/83433* (2013.01); *B29C 66/83435* (2013.01); *A61F 2013/49092* (2013.01); *A61F 2013/51409* (2013.01); *A61F 2013/51449* (2013.01); *B29C 65/1619* (2013.01); *B29C 66/137* (2013.01); *B29C 66/71* (2013.01); *B29C 66/73921* (2013.01); *B29L 2031/4878* (2013.01)

(58) Field of Classification Search
CPC .. A41B 9/00; A41B 9/001; A41B 9/12; B29C 65/02; B29C 65/16; B29C 65/1635; B29C 65/1648; B29C 65/1654; B29C 65/1696; B29C 65/74; B29C 65/741; B29C 65/743; B29C 65/7473; B29C 66/1122; B29C 66/431; B29C 66/4324; B29C 66/723; B29C 66/729; B29C 66/7294; B29C 66/72941; B29C 66/83433; B29C 66/83435

See application file for complete search history.

(56) References Cited

U.S. PATENT DOCUMENTS

| | | | | |
|---|---|---|---|---|
| 4,743,241 | A | * | 5/1988 | Igaue ................. A61F 5/4401 604/385.26 |
| 4,920,575 | A | * | 5/1990 | Bartasis ............... A41D 27/245 2/275 |
| 6,234,229 | B1 | | 5/2001 | Tabuchi |
| 6,387,083 | B1 | * | 5/2002 | Suzuki ................. A61F 13/496 604/385.01 |
| 6,394,991 | B1 | | 5/2002 | Takei et al. |
| 2003/0213552 | A1 | | 11/2003 | Chen et al. |
| 2005/0224472 | A1 | | 10/2005 | Rasmussen et al. |
| 2006/0283846 | A1 | | 12/2006 | Lupinetti et al. |
| 2007/0032766 | A1 | | 2/2007 | Liu et al. |
| 2007/0084553 | A1 | | 4/2007 | Nakajima et al. |
| 2008/0145682 | A1 | | 6/2008 | Rasmussen et al. |
| 2008/0176023 | A1 | | 7/2008 | Bager et al. |
| 2010/0172723 | A1 | * | 7/2010 | Schneider ......... A61F 13/15747 414/222.05 |
| 2012/0021186 | A1 | * | 1/2012 | Schneider ......... A61F 13/15739 428/189 |
| 2012/0095429 | A1 | | 4/2012 | Kobayashi et al. |
| 2013/0068378 | A1 | * | 3/2013 | Dua .................... A43B 1/04 156/243 |
| 2013/0139960 | A1 | | 6/2013 | Maruyama et al. |
| 2013/0174965 | A1 | | 7/2013 | Yamamoto et al. |
| 2015/0064387 | A1 | | 3/2015 | Imai et al. |

FOREIGN PATENT DOCUMENTS

| | | |
|---|---|---|
| CN | 101068519 A | 11/2007 |
| CN | 101237840 A | 8/2008 |
| CN | 101352921 A | 1/2009 |
| CN | 101746057 A | 6/2010 |
| JP | 63-64732 A | 3/1988 |
| JP | 63-118237 A | 5/1988 |
| JP | 64-48690 A | 2/1989 |
| JP | 7-75653 A | 3/1995 |
| JP | 8-38546 A | 2/1996 |
| JP | 9-192863 A | 7/1997 |
| JP | 2000-14697 A | 1/2000 |
| JP | 2001-120595 A | 5/2001 |
| JP | 2001-145659 A | 5/2001 |
| JP | 2004-1507 A | 1/2004 |
| JP | 2004-267335 A | 9/2004 |
| JP | 2005-237768 A | 9/2005 |
| JP | 2008-546540 A | 12/2008 |
| JP | 2009-202502 A | 9/2009 |
| JP | 2009-297300 A | 12/2009 |
| JP | 2010-115849 A | 5/2010 |
| JP | 2010-125654 A | 6/2010 |
| JP | 2010-188629 A | 9/2010 |
| JP | 2011-25006 A | 2/2011 |
| JP | 2011-126011 A | 6/2011 |
| JP | 2011-131556 A | 7/2011 |
| JP | 2012-76343 A | 4/2012 |
| JP | 2012-111076 A | 6/2012 |
| JP | 2012-126130 A | 7/2012 |
| JP | 2013-71282 A | 4/2013 |
| JP | 2013-529149 A | 7/2013 |
| JP | 2013-202182 A | 10/2013 |
| JP | 2013-256109 A | 12/2013 |
| JP | 2013-256133 A | 12/2013 |
| JP | 2014-124398 A | 7/2014 |
| JP | 2014-168904 A | 9/2014 |
| JP | 2015-8944 A | 1/2015 |
| JP | 2015-85091 A | 5/2015 |
| TW | 201201776 A1 | 1/2012 |
| WO | WO 2012/070462 A1 | 5/2012 |
| WO | WO 2013/172343 A1 | 11/2013 |
| WO | WO 2014/103818 A1 | 7/2014 |

OTHER PUBLICATIONS

International Search Report for PCT/JP2014/078296 dated Jan. 20, 2015.
International Preliminary Report on Patentability and English translation of the Written Opinion of the International Searching Authority (Forms PCT/IB/338, PCT/IB/373 and PCT/ISA/237), dated Nov. 27, 2014, for International Application No. PCT/JP2013/063418.
International Search Report (Form PCT/ISA/210), dated Jun. 11, 2013, for International Application No. PCT/JP2013/063418.
Extended European Search Report dated Nov. 2, 2015 for Application No. 13790158.3.
International Preliminary Report on Patentability and English translation of the Written Opinion of the International Searching Authority (forms PCT/IB/373, PCT/ISA/237 and PCT/IB/338), dated Jan. 7, 2016, for International Application No. PCT/JP2014/066923.
International Search Report (form PCT/ISA/210), dated Sep. 22, 2014, for International Application No. PCT/JP2014/066923.

* cited by examiner

Width of Beam Passage Portion: 0.3mm
Spot Diameter of Laser Beam: 0.3mm

Width of Beam Passage Portion: 0.9mm
Spot Diameter of Laser Beam: 0.3mm

Width of Beam Passage Portion: 1.5mm
Spot Diameter of Laser Beam: 0.3mm

Width of Beam Passage Portion: 2.1mm
Spot Diameter of Laser Beam: 0.3mm

Width [mm] of Beam Passage Portion
Spot Diameter of Laser Beam: 0.3mm (Fixed)

PANTS-TYPE WEARING ARTICLE AND PRODUCTION METHOD FOR SAME

TECHNICAL FIELD

The present invention relates to a pull-on garment including side seals and a method for manufacturing the pull-on garment.

BACKGROUND ART

A pull-on disposable diaper, which includes an absorbent assembly and an outer cover forming the outer surface of a garment and in which both lateral side edge portions of the outer cover in a front body portion and both lateral side edge portions of the outer cover in a back body portion are joined to each other to form a pair of side seals, is known as a pull-on garment in the related art.

Generally, when a wearer removes a pull-on disposable diaper from a wearer's body, the wearer pulls the side seal to tear the diaper into the front body portion and the back body portion. It is preferable that the side seal is adapted to be capable of being easily torn in order to promptly remove the diaper from the wearer's body when the wearer replaces a diaper after the use of the diaper. In regard to the tear properties of the side seals, for example, Patent Literature 1 discloses an absorbent article in which sides seals have three stages of fusion-bonding strength in terms of compatibility between sufficient fusion-bonding strength that allows the diaper not to be taken off, when a wearer wears the diaper, and the improvement of tear properties.

Further, in the past, a heat roller device has been widely used for the joining of the superposed sheets in steps of manufacturing an absorbent article, such as a disposable diaper or a sanitary napkin, and side seals have been generally formed by a heat roller device as described below. Further, a method for performing fusion-bonding by using a laser beam is also known as other joining methods. For example, Patent Literature 2 discloses a method for fusion-bonding sheets of a sheet-layered body in which a plurality of sheets are superposed by emitting a laser beam to the sheet-layered body from the inside of a rotating roller while deforming the sheet-layered body into a shape along the circumferential surface of the rotating roller, which includes laser beam transmitting portions on the circumferential surface thereof, and transporting the sheet-layered body.

A pull-on disposable diaper is generally manufactured by the following steps. That is, the pull-on disposable diaper is manufactured by: a step of manufacturing a continuous diaper in which a plurality of diapers are lined up in one direction (transporting direction); a step of joining an outer cover of a front body portion side and an outer cover of a back body portion side, which are superposed at portions where the side seals are to be formed, in the continuous diaper by joining means such as a heat roller device; and a step of dividing the continuous diaper into individual diapers by cutting a joined portion of the outer covers with cutting means such as a cutter. Side seals of a conventional pull-on disposable diaper which is manufactured in this way are formed so that lateral side edge portions of the front body portion and the lateral side edge portions of the back body portion are superposed so as to correspond to each other. Since the apex of the superposed portion further protrudes outward from the peripheral portion of the diaper, the apex of the superposed portion can be easily recognized visually.

CITATION LIST

Patent Literature

Patent Literature 1: JP 2001-120595 A
Patent Literature 2: JP 2010-188629 A
Patent Literature 3: JP 2000-14697 A

SUMMARY OF INVENTION

In recent years, a pull-on disposable diaper has required the same appearance as general underwear. However, since a pull-on disposable diaper includes side seals that are not present on general underwear and the conventional side seals further protrude outward from the peripheral portion of the diaper, the side seals stand out well from the appearance of the diaper. For this reason, it is hard to say that the pull-on disposable diaper has the same appearance as underwear.

Further, since the joining width of the outer cover is large and the outer cover is highly pressurized at the time of joining, the disposed side seals, which are obtained by the above-mentioned manufacturing steps, are likely to be relatively hard. For this reason, there is room for improvement of wearing comfort and the texture of the outer surface.

Further, when a wearer takes off a pull-on absorbent article, such as a pull-on disposable diaper, in order to discard the pull-on absorbent article, the wearer tears the side seals in the longitudinal direction. However, while the wearer tears the side seals in the longitudinal direction, a tear of the sheet may grow in the lateral direction, and the tear of the sheet may reach the inner portion of the diaper than the side seal or may reach the lateral side edge of the diaper. When the lateral tear is formed, it is difficult to smoothly tear the side seal in the longitudinal direction, and for example, a user should apply a force to tear the side seal in the longitudinal direction again. For this reason, effort is required to break the side seal. A method for devising the pattern of the fusion-bonded portion formed on the side seal, and a method for forming a second joined region extending in the vertical direction in parallel with the side seal (see Patent Literature 3) are proposed as a technique for preventing the lateral tear. However, since the width of the side seal is reduced in the method for devising the pattern of the fusion-bonded portion formed on the side seal, it is difficult to make the appearance of the pull-on absorbent article be similar to the appearance of underwear. It is also difficult to make the appearance of the pull-on absorbent article be similar to the appearance of underwear in the method for forming a second joined region.

Accordingly, the invention relates to a pull-on garment that is excellent in appearance, includes side seals excellent in flexibility or texture, and hardly causes lateral tears when the side seals are torn.

The invention provides a pull-on garment that includes an outer cover forming an outer surface of the garment, both lateral side edge portions of the outer cover of a front body portion and both lateral side edge portions of the outer cover of a back body portion being joined to each other to form a pair of side seals, a waist opening, and a pair of leg openings. Each of the side seals includes a seal edge portion where the edge portion of the outer cover of the front body portion and the edge portion of the outer cover of the back body portion are bonded to each other by a continuous linear fusion-bonded portion extending in a longitudinal direction of the side seal. In a cross-section orthogonal to a direction in which the side seal extends, when a direction directed from a side closer to the skin of a wearer toward a side farther from the skin of the wearer of the garment is referred to as an inner-to-outer direction and a direction orthogonal to the inner-to-outer direction is referred to as a thickness direction, the fusion-bonded portion includes a narrow section which is formed at a middle portion thereof in the thickness direction and of which a width along the inner-to-outer direction is small. The narrow section is a section where broad sections are located on both sides of the narrow section in the thickness direction, and the width of the broad section is larger than the width of the narrow section.

Further, the invention relates to a method for manufacturing the pull-on garment. The method for the invention includes: a superposing-pressurizing step of pressurizing a portion, of a continuous outer cover, where a side seal is to be formed in the state that the front body portion side and the back body portion side are superposed; and a side seal-forming step of dividing the outer cover by irradiating the portion, where a side seal is to be formed and which is in the pressurized state, with a laser beam through a beam passage portion, which extends in a direction intersecting a transporting direction of the outer cover, and thereby cutting and separating the outer cover and fusion-bonding the layered outer cover's cut-edge portions that have been formed by the cutting/separation. A support member where a ratio of the width of the beam passage portion to the spot diameter of the laser beam is adjusted so that the fusion-bonded portion including the narrow section and the broad section is formed is used in the side seal-forming step.

DESCRIPTION OF EMBODIMENTS

Figure 1:
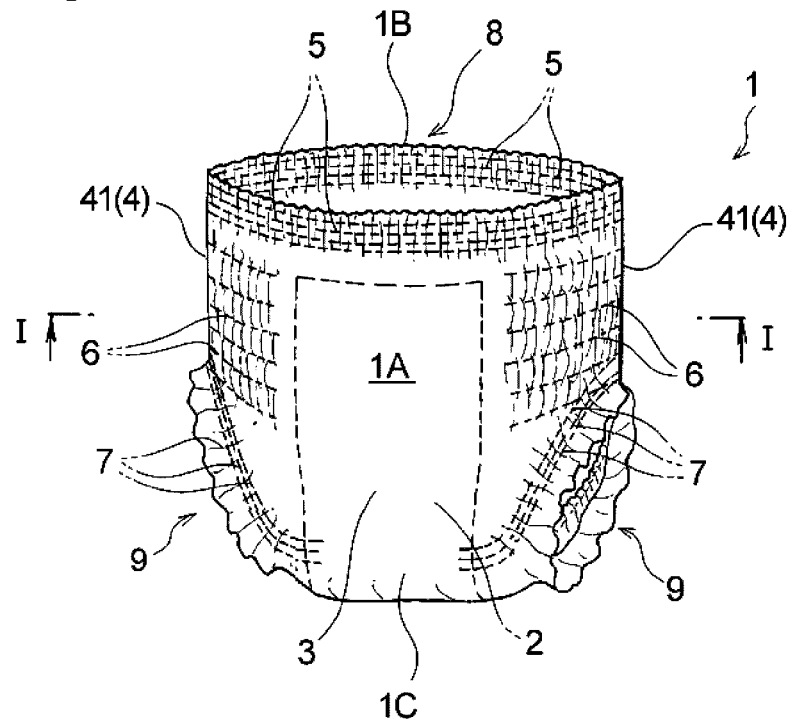
FIG. 1 is a perspective view schematically illustrating a pull-on disposable diaper that is a pull-on garment according to an embodiment of the invention.
Figure 2:
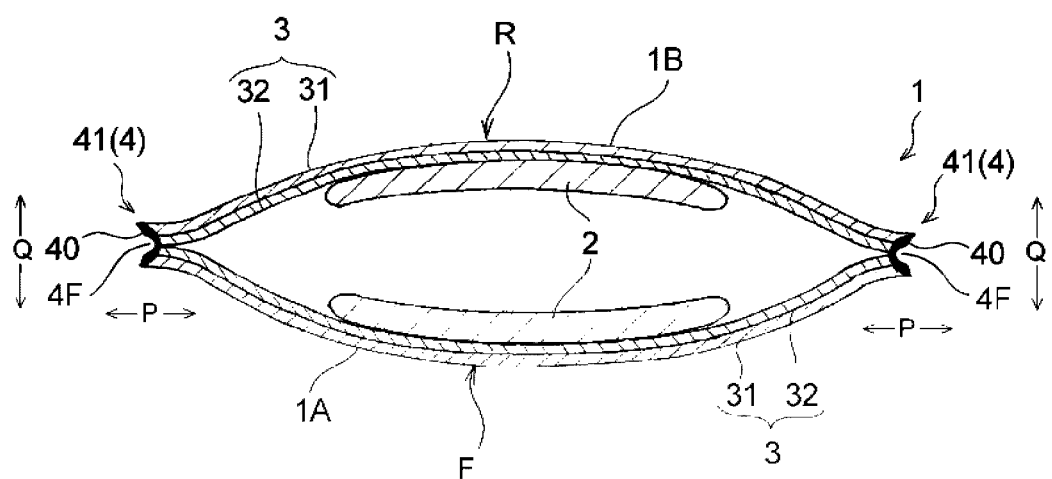
FIG. 2 is a cross-sectional view schematically illustrating a cross-section taken along line I-I of FIG. 1.
Figure 3:
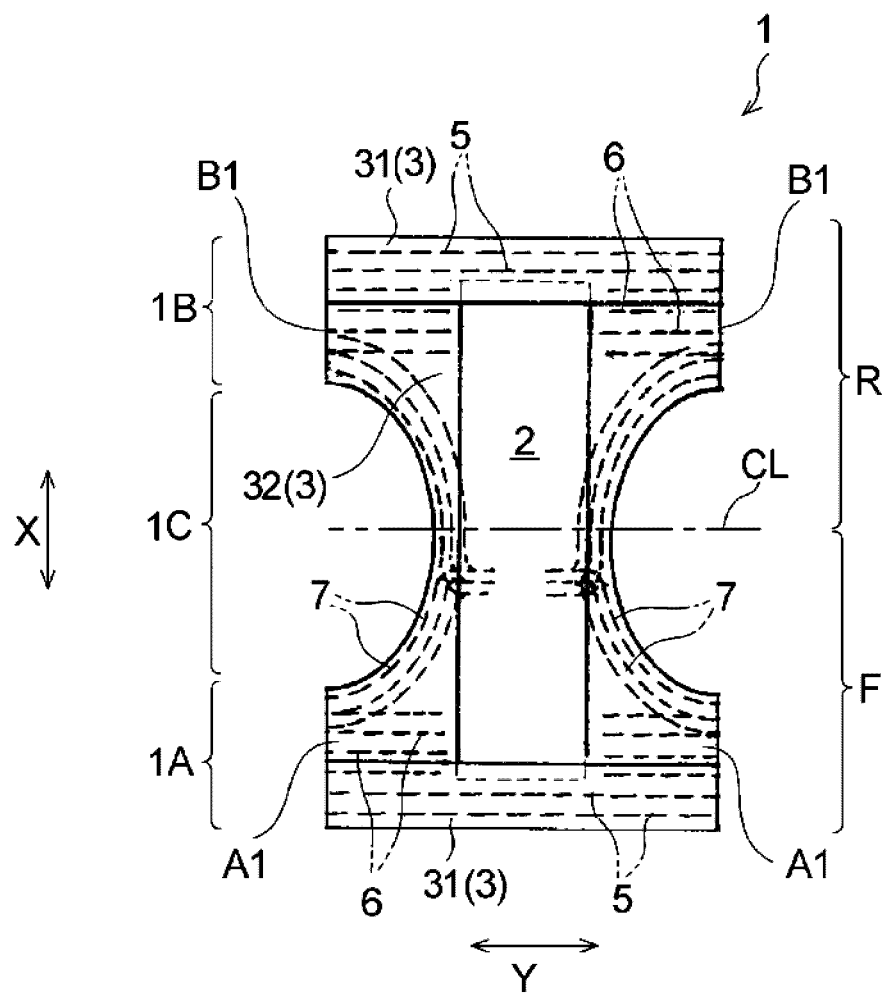
FIG. 3 is a plan view schematically illustrating a state in which the diaper illustrated in FIG. 1 is unfolded and stretched.

The invention will be described below with reference to the drawings on the basis of preferred embodiments thereof. As illustrated in FIGS. 1 to 3, a pull-on disposable diaper 1, which is a pull-on garment according to an embodiment of the invention, is a pull-on disposable diaper that includes an absorbent assembly 2 and an outer cover 3 forming an outer surface of the garment. In the pull-on disposable diaper, both lateral side edge portions A1 and A1, which are along a longitudinal direction X, of the outer cover 3 in a front body portion F (front portion 1A) and both lateral side edge portions B1 and B1, which are along the longitudinal direction X, of the outer cover 3 in a back body portion R (rear portion 1B) are joined to each other to form a pair of side seals 4 and 4, a waist opening 8, and a pair of leg openings 9 and 9. The outer cover 3 is positioned on a non-skin-facing surface side of the absorbent assembly 2 and fixes the absorbent assembly 2.

The diaper 1 has the longitudinal direction X corresponding to a wearer's front-rear direction and a lateral direction Y orthogonal to the longitudinal direction X in a plan view in which the diaper is in an unfolded and stretched state as illustrated in FIG. 3. The diaper 1 can be divided into a crotch portion 1C that is worn about a crotch when a wearer wears the diaper, a front portion 1A that is positioned on the front side of the crotch portion 1C in the longitudinal direction X, and a rear portion 1B that is positioned on the rear side of the crotch portion 1C in the longitudinal direction X. Concave cutout portions, which form the leg openings 9 and 9, are formed at both lateral side edge portions, which are along the longitudinal direction X, of the outer cover 3 in the crotch portion 1C. Further, as illustrated in FIG. 3, the diaper 1 can be divided into the front body portion F and the back body portion R at a virtual center line CL that divides the diaper 1 into two pieces in the longitudinal direction X.

Meanwhile, in this specification, a skin-facing surface is the surface of the pull-on garment or the component thereof (for example, the absorbent assembly) that faces the wearer's skin when a wearer wears the pull-on garment, and a non-skin-facing surface is the surface of the pull-on garment or the component thereof that faces the side (clothing side) opposite to the wearer's skin when a wearer wears the pull-on garment. In the diaper 1, the longitudinal direction X corresponds to a direction (longitudinal direction) along a long side of the disposable diaper or the absorbent assembly 2 that is the component of the disposable diaper, and the lateral direction Y corresponds to the width direction of the disposable diaper or the absorbent assembly 2 that is the component of the disposable diaper.

As illustrated in FIG. 3, the absorbent assembly 2 has an oblong shape that is relatively long in one direction (longitudinal direction X). The absorbent assembly 2 includes a topsheet (not illustrated) that forms the skin-facing surface, a backsheet (not illustrated) that forms the non-skin-facing surface, and a liquid-retentive absorbent member (not illustrated) that is disposed between the topsheet and the backsheet. The absorbent member has a shape that is long in the same direction as the longitudinal direction X. The absorbent assembly 2 is joined to a middle portion of the outer cover 3 by publicly known joining means (adhesive or the like) so that the longitudinal direction of the absorbent assembly 2 corresponds to the longitudinal direction X of the diaper 1 being in an unfolded and stretched state. Here, the unfolded and stretched state means a state in which the side seals are pulled and separated to unfold the diaper and elastic members of each portion are stretched so that the unfolded diaper is stretched up to design dimensions (which are the same dimensions as the dimensions of the diaper that are spread in a planar shape without being affected by elastic members of each portion).

As illustrated in FIGS. 2 and 3, the outer cover 3 includes an outer sheet 31 that forms an outer surface of the diaper 1 (the non-skin-facing surface of the outer cover 3), an inner sheet 32 that is disposed on an inner surface side of the outer sheet 31 and forms an inner surface of the diaper 1 (the skin-facing surface of the outer cover 3), and a plurality of thread-shaped or belt-shaped elastic members 5, 6, and 7 that are fixed between the outer sheet 31 and the inner sheet 32 by an adhesive. The outer sheet 31 and the inner sheet 32 are joined to each other at predetermined portions by an adhesive or heat sealing (not illustrated).

The outer cover 3 (the outer sheet 31 and the inner sheet 32) includes a resin material, and is made of the resin material serving as a main component. Examples of the outer cover 3 (the outer sheet 31 and the inner sheet 32) include a member that includes a thermally fusible synthetic resin, such as polyethylene, polyethylene terephthalate, or polypropylene, as the resin material and is formed of a nonwoven fabric, a film, a layered sheet of a nonwoven fabric and a film, or the like. Examples of the nonwoven fabric include an air-through nonwoven fabric, a heat-rolled nonwoven fabric, a spunlace nonwoven fabric, a spunbond nonwoven fabric, a meltblown nonwoven fabric, and a layered body in which one or two or more of these fabrics are layered so as to form two or more layers.

As illustrated in FIG. 2, the pair of side seals 4 and 4 in the diaper 1 includes seal edge portions 41 where the edge portions of the outer cover 3 in the front body portion F and the edge portions of the outer cover 3 in the back body portion R are bonded to each other by continuous linear fusion-bonded portions 40 extending in the longitudinal direction of the side seal 4. The seal edge portion 41 of the diaper 1 is continuously formed over the entire length of a portion of each of the side seals 4 and 4 between the waist opening 8 and the leg opening 9. The fusion-bonded portion 40 of the seal edge portion 41 is formed by the melting and solidification of resins forming the plurality of sheets (the outer sheet 31 and the inner sheet 32) forming the outer cover 3 while edge portions of these sheets are superposed.

Figure 4:
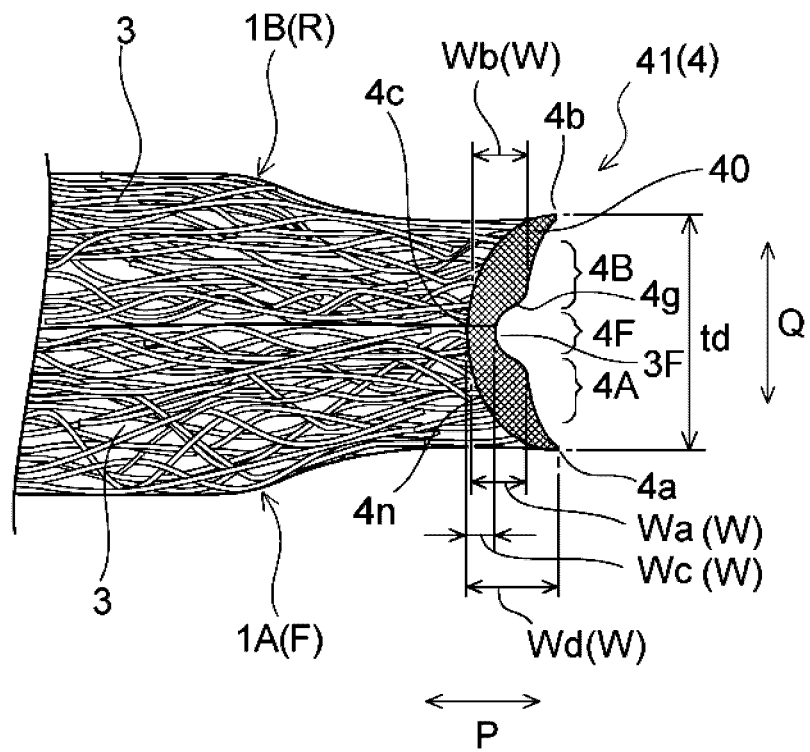
FIG. 4 is a cross-sectional view illustrating a cross-section that illustrates side seals of the diaper illustrated in FIG. 1 and the vicinities of the side seals and is orthogonal to a direction in which the side seals extend.

In a cross-section orthogonal to a direction in which the side seal 4 extends, when a direction directed from a side closer to the skin of a wearer toward a side farther from the skin of the wearer of the garment is referred to as an inner-to-outer direction P and a direction orthogonal to the inner-to-outer direction P is referred to as a thickness direction Q, as illustrated in FIGS. 2 and 4, the fusion-bonded portion 40 of each seal edge portion 41 includes a narrow section 4F which is formed at a middle portion thereof in the thickness direction Q and of which a width W along the inner-to-outer direction P is small, and the narrow section 4F is a section where broad sections 4A and 4B are located on both sides of the narrow section 4F in the thickness direction Q, and the width W of the broad section 4A is larger than the width of the narrow section. When the fusion-bonded portion 40 is divided into five regions in the thickness direction Q so that the entire thickness td of the fusion-bonded portion 40, which is measured after the position of an end 4a of the fusion-bonded portion 40 corresponding to the front body portion F and the position of an end 4b of the fusion-bonded portion 40 corresponding to the back body portion R are aligned with each other in the inner-to-outer direction P, is divided into five equal regions, the middle portion of the fusion-bonded portion 40 in the thickness direction Q corresponds to three middle regions as illustrated in FIG. 4.

As illustrated in FIG. 4, the narrow section 4F of this embodiment is formed at a portion of the fusion-bonded portion 40 where a boundary 3F of the outer cover is present in the thickness direction Q.

Here, as illustrated in FIG. 4, the boundary 3F of the outer cover is a boundary between a portion of the outer cover 3 corresponding to the front body portion F and a portion of the outer cover 3 corresponding to the back body portion R that are fusion-bonded to each other at the fusion-bonded portion 40. The boundary of the outer cover may be adapted so that it is impossible to discriminate the boundary of the outer cover in the fusion-bonded portion 40 or it is difficult to discriminate the boundary of the outer cover in the fusion-bonded portion 40. In this case, the boundary of a portion of the outer cover adjacent to the fusion-bonded portion 40 or a portion of the fusion-bonded portion 40 present on the extension line of the boundary is referred to as the boundary 3F of the outer cover.

As illustrated in FIG. 4, in this embodiment, an outer edge 4g of the fusion-bonded portion 40 in the inner-to-outer direction P has a cross-sectional shape that is dented so as to be convex toward the inside in the inner-to-outer direction P in the cross-section that is orthogonal to the direction in which the side seal 4 extends. In more detail, the outer edge 4g of the fusion-bonded portion 40 includes a high-curvature portion which is formed near a middle portion of the fusion-bonded portion 40 in the thickness direction Q and of which the radius of curvature is smaller than the radii of curvature of other portions of the fusion-bonded portion, and the width W is significantly reduced at a portion of the fusion-bonded portion 40 including the high-curvature portion, so that the above-mentioned narrow section 4F is formed. The inside in the inner-to-outer direction P is a direction which extends toward to the skin of the wearer.

Further, as illustrated in FIG. 4, in this embodiment, an inner edge 4n of the fusion-bonded portion 40 in the inner-to-outer direction P also has a cross-sectional shape that protrudes so as to be convex toward the inside in the inner-to-outer direction P. Accordingly, the fusion-bonded portion 40 has a crescent cross-sectional shape as a whole.

According to the diaper 1 of this embodiment, since the narrow section 4F is provided between the broad section 4A located on the side of the front body portion F and the broad section 4B located on the side of the back body portion R, the fusion-bonded portion 40 is broken at the narrow section 4F and the side seal 4 is reliably torn along the longitudinal direction thereof when the side seal is torn. Accordingly, it is possible to prevent a lateral tear from being formed at the side seal 4. Further, since it is difficult for a lateral tear to be formed at the side seal, according to the diaper 1, it is possible to easily and smoothly remove the diaper after use.

In terms of reliably preventing the lateral tear of the side seal 4, it is preferable that the narrow section 4F is formed at a portion where the boundary 3F of the outer cover is present in the thickness direction Q of the fusion-bonded portion 40 as in this embodiment.

Further, from the same point of view, in the fusion-bonded portion 40, the minimum width Wc of the narrow section 4F is preferably 95% or less of the maximum widths Wa and Wb of the broad sections 4A and 4B provided on both sides of the narrow section 4F, more preferably 90% or less thereof, and preferably 20% or more thereof, more preferably 30% or more thereof, and preferably 20% to 95% thereof, more preferably 30% to 90% thereof.

Furthermore, the minimum width Wc of the narrow section 4F of the fusion-bonded portion 40 is preferably 3 mm or less and more preferably 2 mm or less.

As described above, the side seal 4 of the diaper 1 of this embodiment includes the seal edge portion 41 where the edge portions of the outer cover 3 in the front body portion F and the edge portions of the outer cover 3 in the back body portion R are bonded to each other by the continuous linear fusion-bonded portion 40 extending in the longitudinal direction of the side seal. Accordingly, in comparison with a structure in which a plurality of fusion-bonded portions extending in the width direction of the diaper are formed in the longitudinal direction of the side seal 4 or fusion-bonded portions extending in the width direction of the diaper and fusion-bonded portions extending in the longitudinal direction of the side seal are formed in the form of a lattice, the joining width of a fusion-bonded portion of the outer cover is small and the corners and the like of the fusion-bonded portions do not come into contact with the skin when the side seal is pressed. For this reason, since the side seal is likely to be relatively flexible, the diaper is also excellent in wearing comfort and the texture of the outer surface thereof. Since the length of a portion, which protrudes outward from the waist, of the side seal 4 is short, the diaper is also excellent in appearance.

In terms of the flexibility, the texture, the appearance, and the like of the side seal, the entire width Wd of the fusion-bonded portion 40 in the inner-to-outer direction P is preferably 95% or less of the entire thickness td of the above-mentioned fusion-bonded portion 40, more preferably 50% or less thereof, and preferably 10% or more thereof, more preferably 30% or more thereof, and preferably 10% to 95% thereof, more preferably 30% to 50% thereof.

Further, the entire width Wd of the fusion-bonded portion 40 is preferably 3 mm or less and more preferably 2 mm or less. The entire width Wd of the fusion-bonded portion 40 is a distance, which is measured in the inner-to-outer direction P, between an end 4c of the fusion-bonded portion 40, which is positioned on the innermost side in the inner-to-outer direction P, and the ends 4a and 4b of the fusion-bonded portion 40 that are positioned on the outermost side in the inner-to-outer direction P.

In the diaper 1 of this embodiment, the outer edge 4g of the fusion-bonded portion 40 has a shape that is dented inward in the inner-to-outer direction P. For this reason, when a wearer wears the diaper 1, the visibility of the fusion-bonded portion 40 can deteriorate. Accordingly, the appearance of the diaper 1 becomes more similar to underwear. Furthermore, since the fusion-bonded portion 40 includes the narrow section 4F, the flexibility of the fusion-bonded portion 40 is improved and the texture of the diaper 1 is further softened.

The width W and the entire thickness td of the fusion-bonded portion 40 are measured through the observation of the cross-section of the fusion-bonded portion 40 that is performed at a magnification of 50 to 200× by a microscope (trade name: VHX-1000 manufactured by KEYENCE Corporation) under conditions in which the front portion 1A and the rear portion 1B are superposed as illustrated in FIG. 4 but a load is not applied. Further, the width W and the entire thickness td of the fusion-bonded portion 40 are measured after the position of the end 4a of the fusion-bonded portion 40 located on the side of the front body portion F and the position of the end 4b of the fusion-bonded portion 40 located on the side of the back body portion R are aligned with each other in the inner-to-outer direction P as illustrated in FIG. 4.

It is preferable that the mean values of measured values of the width W, the entire thickness td, and the like, which are measured in the cross-sections at different three or more positions in the direction along the side seal 4, are used as the width W, the entire thickness td, and the like; and it is preferable that the respective dimensions are measured to two decimal places.

The above-mentioned diaper 1 can be manufactured by, for example, a manufacturing method to be described below that is a method for manufacturing a pull-on garment according to an embodiment of the invention.

A method for manufacturing the diaper 1 of this embodiment includes: a superposing-pressurizing step of pressurizing a portion, of a continuous outer cover 3, where a side seal is to be formed in the state that the front body portion side and the back body portion side are superposed; and a side seal-forming step of dividing the outer cover 3 by irradiating the portion, where a side seal 4 is to be formed and which is in the pressurized state, with a laser beam through a beam passage portion 27, which extends in a direction intersecting a transporting direction A of the outer cover 3, and thereby cutting and separating the outer cover and fusion-bonding the layered outer cover's cut-edge portions that have been formed by the cutting/separation. Further, the method includes an assembly fixing step of fixing the absorbent assembly 2 to the continuous outer cover 3 (the outer sheet 31 and the inner sheet 32) before the superposing-pressurizing step.

Figure 5:
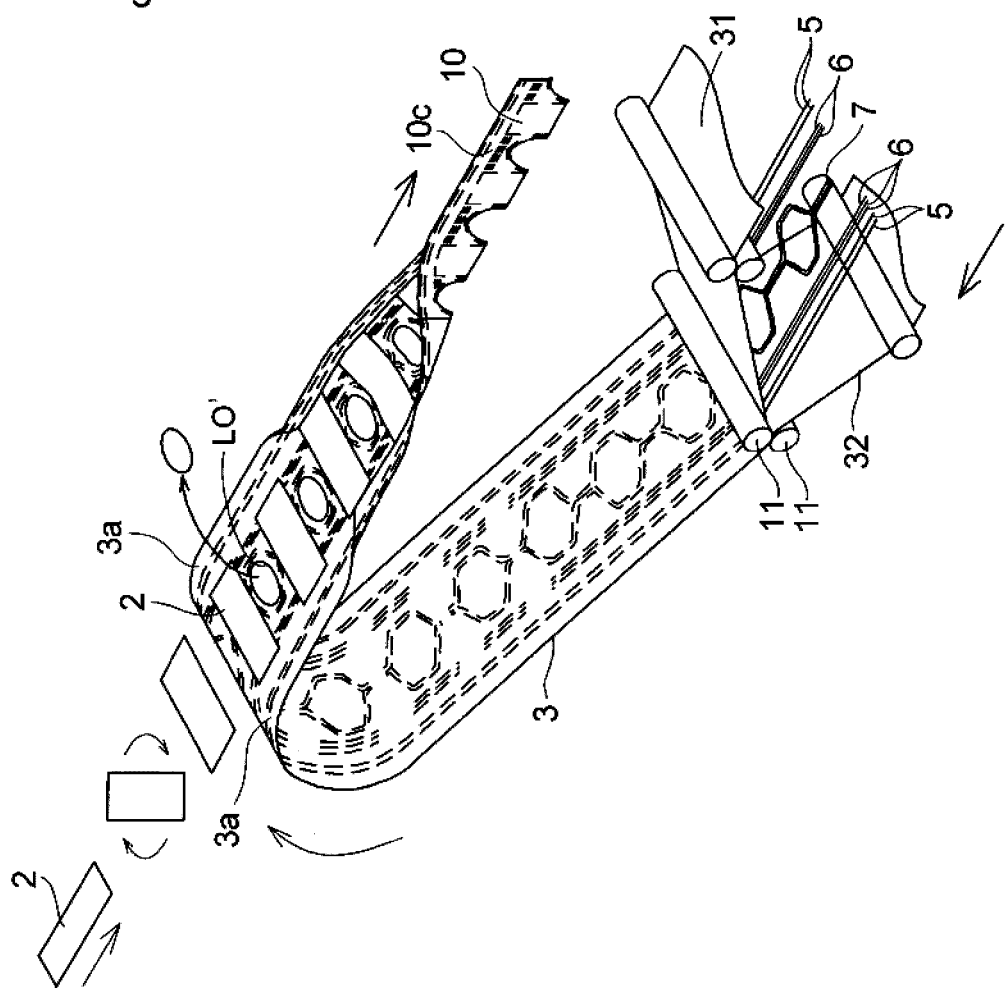
FIG. 5 is a perspective view schematically illustrating steps of manufacturing a continuous diaper in the manufacture of the diaper illustrated in FIG. 1.
Figure 6:
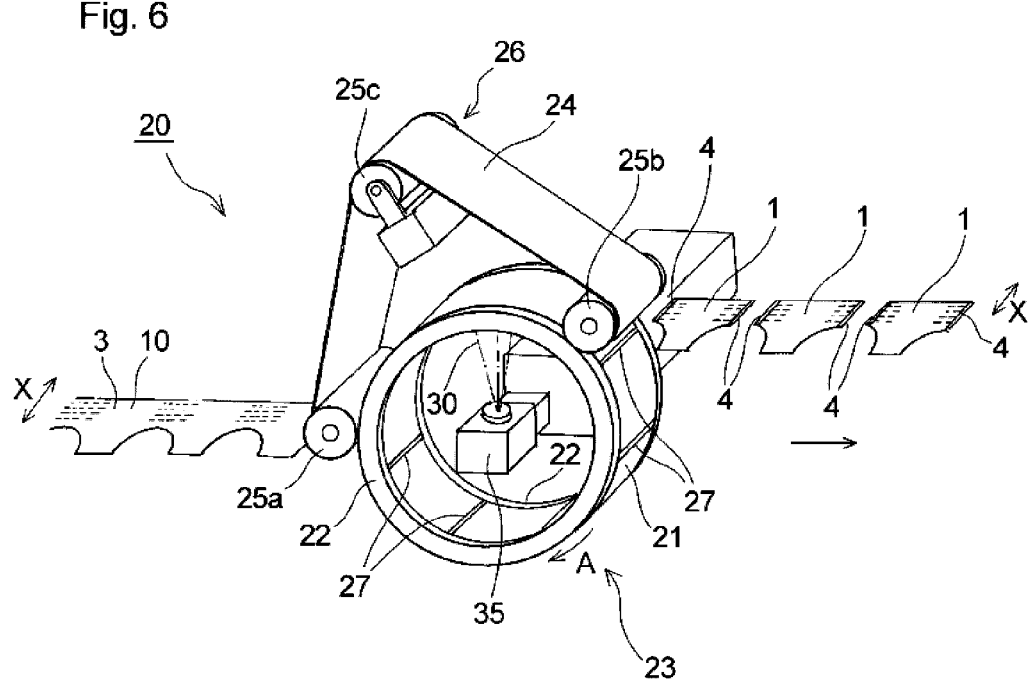
FIG. 6 is a perspective view illustrating a laser type joining device that is preferably used to manufacture the pull-on garment of the invention and an aspect in which a continuous diaper is fusion-cut by the laser type joining device.

More specifically, as illustrated in FIG. 5, in the superposing-pressurizing step of the method for manufacturing the diaper 1, the continuous outer cover 3 (the outer sheet 31 and the inner sheet 32) is folded in the width direction thereof so that the front body portion side and the back body portion side of the continuous outer cover 3 to which the absorbent assembly 2 is fixed are superposed. Accordingly, "a continuous diaper 10 in which precursors of pull-on disposable diapers not provided with side seals are lined up in one direction" is manufactured. Then, as illustrated in FIG. 6, in the side seal-forming step, the continuous outer cover 3 of the continuous diaper 10 is divided (fusion-cut) into individual pieces by the irradiation of a laser beam 30 and cut edge portions, which are formed by the division of the continuous outer cover, of a plurality of layered outer covers 3 (the outer sheet 31 and the inner sheet 32) are fusion-bonded to each other, so that a pull-on disposable diaper 1 including the outer cover 3 including the pair of side seals 4 and 4 is continuously manufactured.

In more detail, first, as illustrated in FIG. 5, a plurality of waist-elastic members 5 forming waist gathers, a plurality of below-waist elastic members 6 forming below-waist gathers, and a plurality of leg-elastic members 7 forming leg gathers are disposed between a continuous outer sheet 31 that is continuously fed from a raw fabric roll (not illustrated) and a continuous inner sheet 32 that is continuously fed from a raw fabric roll (not illustrated), so as to be stretched at a predetermined elongation rate. In this case, the leg-elastic members 7 are disposed so as to form a predetermined leg pattern by a known oscillation guide (not illustrated) which reciprocates in a direction orthogonal to the flow direction of a sheet. Further, before the continuous outer sheet 31 and the continuous inner sheet 32 are superposed, a hot-melt adhesive is applied to predetermined portions on one or both of the surfaces, which face each other, of the continuous outer sheet 31 and the continuous inner sheet 32 by an adhesive coater (not illustrated). Meanwhile, when elastic members, such as the waist-elastic members 5 and the below-waist elastic members 6, are disposed in the stretched state so as to cross portions, which are to be divided by the irradiation of a laser beam, (portions where the side seals 4 are to be formed, portions to be divided denoted by reference numeral 10C of FIG. 7) of both the continuous outer sheet 31 and the continuous inner sheet 32, it is preferable that an adhesive is applied to the portions or the vicinities thereof to avoid troubles, such as the significant contraction of the divided elastic members or the separation of the elastic members. Before the waist-elastic members 5 and the below-waist elastic members 6 are disposed between the continuous outer sheet 31 and the continuous inner sheet 32, a hot-melt adhesive may be intermittently applied to the waist-elastic members 5 and the below-waist elastic members 6 by an adhesive coater (not illustrated).

Then, as illustrated in FIG. 5, the continuous outer sheet 31 and the continuous inner sheet 32 between which the waist-elastic members 5, the below-waist elastic members 6, and the leg-elastic members 7 are interposed in the stretched state are fed to a gap between a pair of nip rollers 11 and 11 and are pressurized. As a result, a continuous outer cover 3 in which the plurality of elastic members 5, 6, and 7 are disposed in the stretched state between the continuous outer sheet 31 and the continuous inner sheet 32 is formed.

In the step of forming the outer cover 3, it is also preferable that a plurality of joined regions (not illustrated) where the continuous outer sheet 31 and the continuous inner sheet 32 are joined to each other are formed between two adjacent below-waist elastic members 6 and 6 by joining means (not illustrated), such as a convex roller and an anvil roller corresponding to the convex roller.

After that, as necessary, the plurality of below-waist elastic member 6 and the plurality of leg-elastic members 7 are pressed and cut into a plurality of pieces without causing contraction by elastic member-precutting means (not illustrated) so as to correspond to a position where an absorbent assembly 2 to be described below is to be disposed. Examples of the elastic member-precutting means include elastic member dividing portions, which are used in a method for manufacturing a composite elastic member disclosed in JP 2002-253605 A, and the like.

Next, as illustrated in FIG. 5, an adhesive, such as a hot-melt adhesive, is applied (not illustrated) to the absorbent assemblies 2, which have been manufactured in another step, in advance and the absorbent assemblies 2 are rotated by an angle of 90° and are intermittently fed and fixed to the inner sheet 32 of the continuous outer cover 3 (an assembly fixing step). Meanwhile, the adhesive for fixing the absorbent assembly may not be applied to the absorbent assemblies 2 and may be applied to portion of the inner sheet 32 where the absorbent assemblies 2 are to be disposed in advance.

Then, as illustrated in FIG. 5, a leg hole LO' is formed in an annular portion, which is annularly surrounded by the leg-elastic member 7, of the continuous outer cover 3 on which the absorbent assembly 2 is disposed. The step of forming the leg hole can be performed by using the same means as means, such as a rotary cutter or a laser cutter, which has been used in a method for manufacturing this kind of article in the related art. Meanwhile, in the embodiment illustrated in the drawings, the leg hole has been formed after the absorbent assembly 2 is disposed on the continuous outer cover 3. However, the leg hole may be formed before the absorbent assembly 2 is disposed.

After that, the continuous outer cover 3 is folded in the width direction thereof (a direction orthogonal to the transporting direction of the outer cover 3). More specifically, as illustrated in FIG. 5, after both lateral side portions 3a and 3a, along the transporting direction, of the continuous outer cover 3 are folded so as to cover both longitudinal ends of the absorbent assemblies 2 and fix both the longitudinal ends of the absorbent assemblies 2, the outer cover 3 is folded in half in the width direction thereof together with the absorbent assemblies 2 (a superposing step of the superposing-pressurizing step). The continuous diaper 10 is obtained in this way.

The continuous diaper 10 includes: the continuous outer cover 3 of which the front body portion side and the back body portion side are superposed; and the absorbent assemblies 2 that are intermittently fixed to the continuous outer cover 3. The continuous diaper 10 and the continuous outer cover 3 include the portions 10C, where the side seals 4 are to be formed, between the absorbent assemblies 2 and 2 in the transporting direction. At the portions 10C, where the side seals are to be formed, the front body portion side and the back body portion side of the continuous outer cover 3 are directly superposed without the absorbent assembly 2 interposed therebetween. The continuous outer cover 3 of the continuous diaper 10 also corresponds to "the continuous outer cover of which the front body portion side and the back body portion side are superposed".

Next, as illustrated in FIG. 6, a pair of side seals 4 and 4 is formed by irradiating the continuous diaper 10, which is manufactured in this way, with a laser beam by a laser type joining device 20 (the side seal-forming step), so that a pull-on disposable diaper 1 including the outer cover 3 having the pair of side seals 4 is continuously manufactured. As illustrated in FIG. 7, in the manufacturing method for this embodiment, a pair of side seals 4 and 4, which forms side seals of two diapers (pull-on garments), is formed at each of the portions 10C, where the side seals are to be formed, of "the continuous outer cover in which the front body portion side and the back body portion side are superposed" which forms a part of the continuous diaper 10.

The laser type joining device 20 will be described. As illustrated in FIG. 6, the laser type joining device 20 includes: a hollow cylindrical roller 23 that is rotationally driven in the direction of an arrow A; an irradiation head 35 that is disposed in a hollow portion of the cylindrical roller 23 and emits a laser beam 30 toward a cylindrical support member 21 which forms the peripheral surface of the cylindrical roller 23; and a belt type pressurizing unit 26 that includes an endless pressurizing belt 24 (a pressing member).

The laser type joining device 20 includes a tension adjustment mechanism (not illustrated) that can increase and reduce (adjusts) the tension of the pressurizing belt 24 wound on the outer peripheral surface of the annular support member 21 (the peripheral surface of the cylindrical roller 23), and can appropriately adjust the pressure applied to the continuous diaper 10 (a sheet-layered body) through the adjustment of the tension by the support member 21 and the pressurizing belt 24.

The support member 21 forms the peripheral surface (a portion coming into contact with a workpiece) of the cylindrical roller 23, and is interposed and fixed between a pair of frames 22 and 22 that forms both ends of the cylindrical roller 23 in the direction of the axis of rotation of the cylindrical roller 23. The support member 21 is made of a metal material, such as iron, aluminum, stainless steel, or copper, or a heat-resistant material such as ceramics.

The support member 21 includes beam passage portions 27 through which a laser beam can pass. As illustrated in FIG. 6, the support member 21 includes slit-like openings 27, which penetrate the support member 21 in the thickness direction, as the beam passage portions. Each of the openings 27 has a rectangular shape in a plan view, and the plurality of openings 27 are formed at predetermined intervals in the circumferential direction of the cylindrical support member 21 so that the longitudinal direction of each opening corresponds to the direction crossing the transporting direction A of the continuous diaper 10 (the continuous outer cover 3), more specifically, a direction parallel to the axis of rotation of the cylindrical roller 23. The support member 21 allows a laser beam to pass therethrough at the openings 27, but does not allow a laser beam to pass (transmit) therethrough at portions other than the openings 27. Examples of a method for forming the openings 27 at the support member 21 include 1) a method for forming openings 27 at predetermined portions of a support member 21, which is formed of a single annular member having the same length as the circumferential length of an annular frame 22, by etching, punching, laser machining, or the like; and 2) a method for using a plurality of curved rectangular members as a support member 21 instead of a single annular member and arranging the plurality of members between a pair of frames 22 and 22 at predetermined intervals in the circumferential direction of the frame 22.

In the laser type joining device 20, the beam passage portions through which a laser beam can pass are formed of the slit-like openings 27 that penetrate the support member 21 in the thickness direction. Accordingly, when the pressurizing belt 24 comes into contact with the portions of the continuous diaper 10 that are superposed on the openings 27 (the portions 10C to be divided), the portions of the continuous diaper 10 that are superposed on the openings 27 (the portions 10C to be divided) are not sandwiched between the support member 21 and the pressurizing belt 24 (the pressing member). Accordingly, strictly speaking, a pressing force, which is generated when the portions 10C to be divided are sandwiched between the support member 21 and the pressurizing belt 24, is not generated at the portions 10C to be divided. However, since the vicinities of the portions 10C to be divided, that is, portions of the continuous diaper 10 superposed on the vicinities of the openings 27 (opening-edge portions) are sandwiched between the support member 21 and the pressurizing belt 24 even though the portions 10C to be divided superposed on the openings 27 are not sandwiched between the support member 21 and the pressurizing belt 24, the portions 10C to be divided are not moved before and after the irradiation of a laser beam. Accordingly, the cut edge portions, which are formed by the division of the continuous diaper 10 caused by the irradiation of a laser beam, are not moved. That is, the portions 10C to be divided of the continuous diaper 10 (portions of the sheet-layered body superposed on the openings 27) are portions restrained by a pressing force that is generated when the portions are interposed between the support member 21 and the pressurizing belt 24; and are portions that are actually affected by the pressing force.

The belt type pressurizing unit 26 includes the endless pressurizing belt 24 (the pressing member) and three rollers 25a, 25b, and 25c that are rotated while the pressurizing belt 24 is wound on the three rollers 25a, 25b, and 25c. The rollers 25a, 25b, and 25c may be driving rollers, or may be driven rollers that are rotated by the pressurizing belt 24. The pressurizing belt 24 is moved at the same speed as the cylindrical roller 23 (the support member 21) by one or more of the rollers 25a, 25b, and 25c as driving rollers or while being rotated by the cylindrical roller 23. It is preferable that the temperature of the support member 21 and the temperature of the pressurizing belt 24 are maintained in a predetermined temperature range by air cooling, water cooling, or the like.

A belt made of metal or a resin, which has heat resistance for resisting heat generated during machining, can be used as the pressurizing belt 24 (the pressing member). For example, a belt made of a metal material, such as iron, aluminum, or stainless steel, can be used as the pressurizing belt 24. Further, a belt, which does not have transmissivity for a laser beam irradiating the workpiece (the continuous outer cover 3), is generally used as the pressurizing belt 24, but a belt having the transmissivity can also be used as the pressurizing belt 24.

As illustrated in FIG. 6, the irradiation head 35, which emits a laser beam 30 toward the support member 21 forming the peripheral surface of the cylindrical roller 23, is provided in the hollow portion of the hollow cylindrical roller 23. The irradiation head 35 is a galvano scanner (a device in which mirrors are mounted on a shaft of a motor) that freely scans an object with a laser beam 30. The irradiation head 35 includes: a mechanism that makes the laser beam 30 move to and fro in a direction parallel to the rotation axis of the cylindrical roller 23; a mechanism for moving, in the circumferential direction of the cylindrical roller 23, the position (irradiation point) where the laser beam 30 is incident on the continuous diaper strip 10 on the support member 21; and a mechanism for keeping the spot diameter of the laser beam 30 constant on the peripheral surface of the cylindrical roller 23; and the like. With this configuration, the laser irradiation mechanism can move the irradiation point of the laser beam 30 discretionarily in both the circumferential direction of the cylindrical roller 23 and a direction orthogonal to the circumferential direction.

As illustrated in FIG. 6, the continuous diaper 10 is introduced onto the outer surface of the support member 21, which forms the peripheral surface of the cylindrical roller 23 rotationally driven in a direction of an arrow A, by guide rollers (not illustrated) and the like while predetermined tension is applied to the continuous diaper 10. After the continuous diaper 10 is wound on the support member 21 and is conveyed by a predetermined distance in the circumferential direction of the cylindrical roller 23 through the rotation of the cylindrical roller 23, the continuous diaper 10 is separated from the support member 21 by an outlet roller and nip rollers, which are not illustrated, and the like. As described above, the continuous diaper 10 is wound on the support member 21, which forms the peripheral surface of the cylindrical roller 23, with predetermined tension and is conveyed while coming into pressure contact with the pressurizing belt 24. Accordingly, the portions of the continuous diaper 10 that are sandwiched between the support member 21 and the pressurizing belt 24 and the vicinities thereof have been pressurized (compressed) in the thickness direction thereof before the continuous diaper 10 is divided by being irradiated with a laser beam. For this reason, it is possible to more efficiently compress the continuous diaper 10 in a case that the continuous diaper 10 contains a nonwoven fabric. As a result, when the compressed continuous diaper 10 is divided by being irradiated with a laser beam, it is possible to more reliably fusion-bond the cut edge portions of the plurality of sheets (the outer cover 3) forming the divided portions. Accordingly, the fusion-bonding strength of the side seal 4 is improved.

The rotation angle of the support member 21 (cylindrical roller 23), which is rotated until the continuous diaper 10 is separated from the support member 21 after the continuous diaper 10 is introduced onto the support member 21, can be in the range of, for example, 90° to 270° and more preferably in the range of 120° to 270°. Further, assuming that the pressure contact angle is 360° when the continuous diaper 10 comes into pressure contact with the support member 21 over the entire circumference of the cylindrical support member 21 (the cylindrical roller 23) in the circumferential direction, the range of an angle (a pressure contact angle), which allows the continuous diaper 10 to come into pressure contact with the support member 21 by the pressurizing belt 24 (the pressing member), is preferably the range of 90° to 270° and more preferably the range of 120° to 270°.

In the embodiment illustrated in FIG. 6, while the continuous diaper 10 is continuously conveyed, a first surface 10a of the continuous diaper 10 comes into contact with the outer surface of the support member 21 that forms the peripheral surface of the cylindrical roller 23 and includes slit-like openings 27 (the beam passage portions) through which a laser beam 30 can pass. As a result, the continuous diaper 10 (the portions where the side seals 4 are to be formed) are pressurized by the support member 21 and the pressurizing belt 24 (the pressing member). The compressed continuous diaper 10 is divided by being irradiated with a laser beam 30 emitted from the support member 21 side through the openings 27, and cut edge portions, which are formed by the division, of the plurality of sheets (the outer cover 3), which are pressurized, are fusion-bonded to each other, so that the side seal 4 is formed (the side seal-forming step).

FIG. 7 is a diagram illustrating an aspect in which the continuous diaper 10 (the continuous sheet laminate) is divided and, at the same time, the side seals 4 (seal edge portions) are formed by the laser type joining device 20. FIG. 7(*a*) schematically illustrates the portion 10C to be divided (the portion where the side seals 4 are to be formed) of the continuous diaper 10 that are to be divided by a laser beam 30 and the vicinity thereof. The portion 10C to be divided of the continuous diaper 10 of the illustrated aspect is a middle, in the longitudinal direction (the transporting direction A), of a region of the continuous diaper 10 in which the absorbent assembly 2 is not disposed. Each of an end of the waist opening 8 (see FIG. 1) of the portion 10C to be divided and the vicinity thereof are formed of an eight-layer structural portion in which eight sheets are superposed, and each of other portions of the portion 10C to be divided is formed of a four-layer structural portion in which four sheets are superposed. As illustrated in FIG. 7(*a*), the four-layer structural portion includes two sheets (the outer sheet 31 and the inner sheet 32) of one outer cover 3 in the front portion 1A and two sheets 31 and 32 of one outer cover 3 in the rear portion 1B, and has a structure in which these four sheets are layered. Meanwhile, since both lateral side portions 3a and 3a of the continuous outer cover 3 are folded to cover the both longitudinal ends of the absorbent assembly 2 during the manufacture of the continuous diaper 10 as described above (see FIGS. 3 and 5), two outer covers 3 present in each of the front portion 1A and the rear portion 1B, that is, a total of four outer covers 3 and 3 are layered at the eight-layer structural portion. As a result, the eight-layer structural portion has a structure in which eight sheets 31 and 32 are layered. Meanwhile, there is a case in which elastic members, such as the waist-elastic members 5 and the below-waist elastic members 6, are disposed between the sheets 31 and 32 superposed in each of the four-layer structural portion and the eight-layer structural portion. The four-layer structural portion will be mainly described below, but the eight-layer structural portion is also provided with the side seals 4 having the same structure as the side seals of the four-layer structural portion unless otherwise stated.

In the portion 10C, which is to be divided and which has a four-layer structure, of the continuous diaper 10, one or both of the outer sheet 31, which forms the first surface 10a (the surface coming into contact with the support member 21) of the continuous diaper 10 and the sheet (the inner sheet 32) other than the sheet, which forms the first surface 10a, are sheets that can generate heat by absorbing a laser beam 30. In the illustrated aspect, all four of the outer sheet 31 and the inner sheet 32 forming the portion 10C to be divided are sheets (nonwoven fabrics) that can generate heat by absorbing a laser beam 30. Further, the two sheets, that is, the outer sheet 31 and the inner sheet 32, which are superposed in the portion 10C to be divided, and in the vicinity thereof, may be joined to each other by an adhesive or the like or may not be joined to each other at all before the irradiation of a laser beam 30.

As illustrated in FIG. 7(*b*), the continuous diaper 10 is introduced onto the support member 21 rotating in the direction of an arrow A in such a manner that the first surface 10a comes into contact with the support member 21 and the portion 10C is to be divided (the portion where the side seals 4 are to be formed) is positioned on the slit-like opening 27; and the pressurizing belt 24 (the pressing member) is pressed against a second surface 10b; so that the continuous diaper 10 is pressurized (compressed) in the thickness direction while being conveyed in the direction of the arrow A. Then, the portion 10C to be divided which is conveyed and is pressurized is irradiated with a laser beam 30 emitted from the support member 21 side through the opening 27. As described above, the irradiation point of a laser beam 30 is adapted to be capable of arbitrarily moving in the circumferential direction of the cylindrical roller 23, and is set so that scanning is performed while following the movement of the opening 27 in the circumferential direction. Accordingly, the portion 10C to be divided, which is positioned on the opening 27, is continuously irradiated with a laser beam 30 for a predetermined time during conveying.

When the portion 10C, which is to be divided and which has a four-layer structure is irradiated with a laser beam 30, the materials (fibers or the like) of the outer sheet 31 and the inner sheet 32 present in the portion 10C to be divided gasify and disappear due to heat generated by a direct irradiation of the laser beam 30 and the materials present in the vicinity of the portion 10C to be divided are indirectly heated and melted by a laser beam 30. As a result, as illustrated in FIG. 7(*c*), the portion 10C, which is to be divided and which has a four-layer structure, is melted and cut, and the continuous diaper 10 is divided so that a single sheet laminate (a diaper precursor) is separated from the continuous diaper 10; and cut edge portions of four sheets 31 and 32 of the sheet laminate as well as cut edge portions of the four sheets 31 and 32 of the separated continuous diaper 10, which are formed by the division of the continuous diaper 10, are fusion-bonded to each other. These cut edge portions have been pressurized (compressed) by sandwiching between the support member 21 and the pressurizing belt 24 before the cut edge portions are formed (before the continuous diaper 10 is divided by being irradiated with a laser beam 30). According to the method for manufacturing a diaper of the illustrated aspect, as described above, the division of the continuous outer cover 3 and the fusion-bonding of the two cut edge portions of the pressurized outer cover 3, which are formed by the division of the continuous outer cover 3, are simultaneously performed by the single irradiation of a laser beam. Accordingly, since it is possible to perform the fusion-bonding and division in single step with substantially a half of a laser output in comparison with a method for fusion-bonding two portions by two times of the irradiation of a laser beam, it is possible to efficiently manufacture the diaper 1.

Figure 7A:
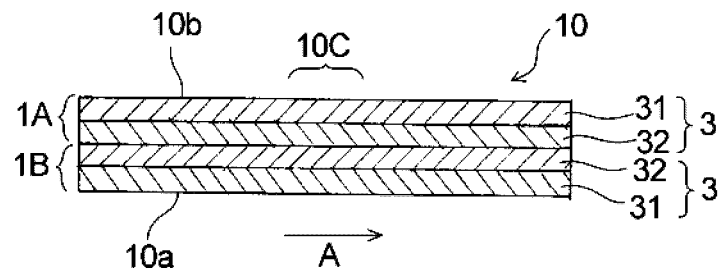
FIGS. 7(a) to 7(c) are diagrams illustrating an aspect in which the continuous diaper (continuous outer cover) is divided and, at the same time, the side seals (seal edge portions) are formed by the laser type joining device illustrated in FIG. 6.
Figure 7B:
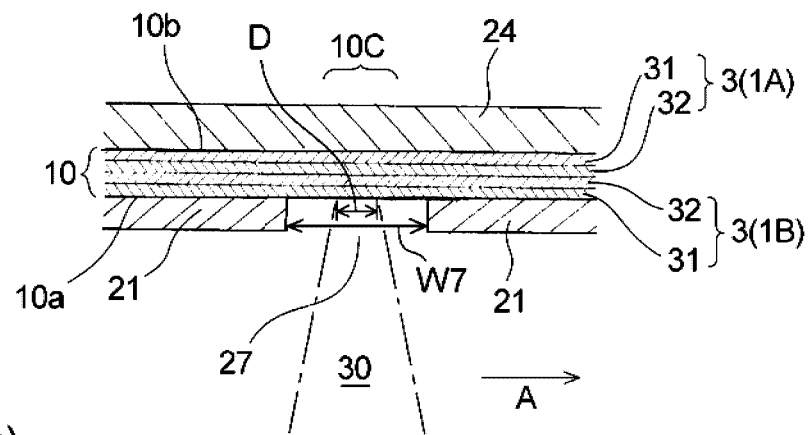
Figure 7C:
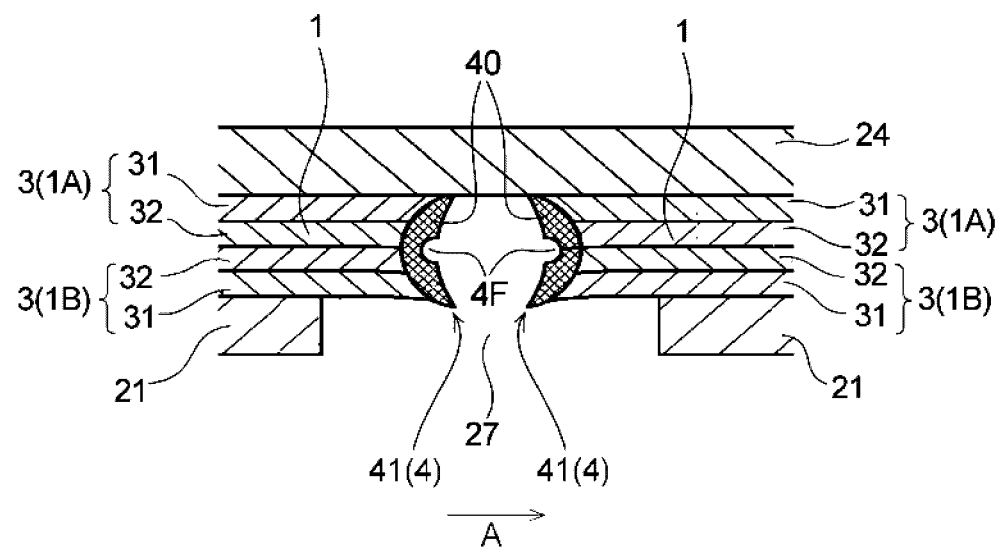

In the manufacturing method for this embodiment, as illustrated in FIG. 7(c), the width W7 of the slit-like opening 27 (see FIG. 7(b), the length of the opening 27 in the circumferential direction of the cylindrical roller 23) is set to be larger than the spot diameter D of a laser beam 30 so that the above-mentioned narrow section 4F is formed at the fusion-bonded portion 40. However, the outer cover 3 located on the side of the front body portion F and the outer cover 3 located on the side of the back body portion R are not joined to each other when the width W7 of the opening 27 is too larger than the spot diameter D of a laser beam 30. Therefore, it is important to set a ratio of the width W7 to the spot diameter D in an appropriate range. Further, this appropriate range is affected by the irradiation intensity of a laser beam, the material of a sheet, the number of layered sheets. Accordingly, after a preliminary test using an outer cover used for the front body portion and the back body portion of the diaper 1 is performed to investigate a ratio of the width of the opening 27 to the spot diameter D of a laser beam 30 that allows a preferred narrow section 4F to be formed, it is preferable that the diapers 1 are continuously produced under the appropriate condition for the preferred narrow section 4F.

FIG. 8 illustrates the investigation results of a spot diameter, the width of a slit-like opening (a beam passage portion), and the shape of a fusion-bonded portion formed in the case that a continuous outer cover in which four nonwoven fabrics made of a polypropylene fiber are superposed (a hot-melt adhesive is interposed between the nonwoven fabrics) is irradiated with a laser beam under the following conditions while being pressurized by the laser type joining device illustrated in FIG. 6.

Figure 8A:
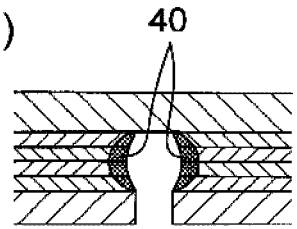
FIGS. 8(a) to 8(d) are schematic views illustrating the change of the pressurized state of a target portion to which a laser beam is to be applied and the change of the form of a fusion-bonded portion to be formed when a ratio of the width of a slit-like opening (beam passage portion) to the spot diameter of a laser beam is changed.
Figure 8B:
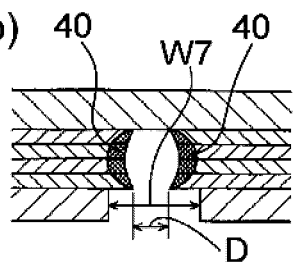

Irradiation Conditions of Laser Beam
Spot diameter: 0.3 mm
Pressure: 0.4 MPa
Laser output: 24 W
Scanning speed: 325 mm/sec When the spot diameter of a laser beam and the width of the beam passage portion are equal to each other or when the width of the beam passage portion is about three times the spot diameter of a laser beam as illustrated in FIG. 8(b), a fusion-bonded portion 40 including a narrow section 4F is less likely to be formed. However, when the width of the beam passage portion (the slit-like opening) is five or seven times the spot diameter of a laser beam as illustrated in FIG. 8(c) or 8(d), fusion-bonded portions 40 including narrow sections 4F are formed.

Figure 8C:
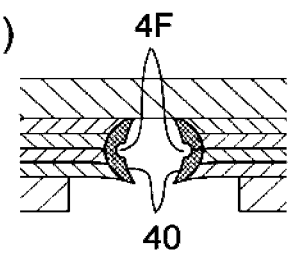
Figure 8D:
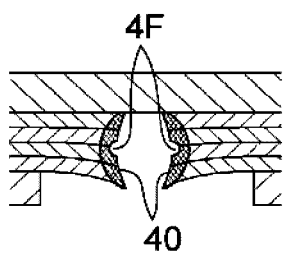
Figure 9:
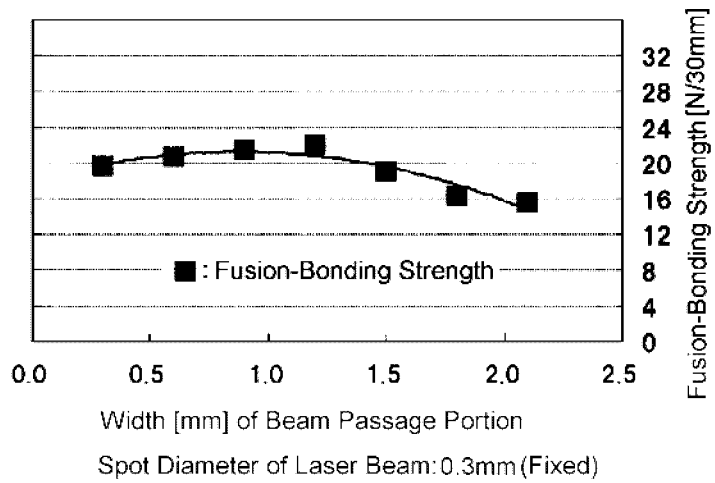
FIG. 9 is a graph illustrating the change of fusion-bonding strength when the width of the slit-like opening (beam passage portion) is changed with respect to the spot diameter of a laser beam.

Meanwhile, FIG. 9 is a graph illustrating a relationship between the width of the beam passage portion and the fusion-bonding strength of a side seal when fusion-bonded portions are formed in the same manner as the test of FIG. 8 while the width of the beam passage portion is changed and the spot diameter is constant.

As apparent from the graph illustrated in FIG. 9, it is found that sufficient fusion-bonding strength is obtained when the width of the beam passage portion is set to five times the spot diameter of a laser beam and the narrow section 4F is formed at the fusion-bonded portion 40 as illustrated in FIG. 8(c). Further, as illustrated in FIG. 8(d), when the width of the beam passage portion is set to seven times the spot diameter, fusion-bonded portions including narrow sections are formed but the fusion-bonding strength is slightly lower than the fusion-bonding strength that is obtained in the case that the width of the beam passage portion is set to five times the spot diameter.

From these results, it is found as follows: it is preferable that the width of the beam passage portion (the slit-like opening) is set to be larger than the spot diameter of a laser beam 30 when a fusion-bonded portion including a narrow section is formed by this embodiment or a similar method, but it is preferable that a ratio of the width of the beam passage portion to the spot diameter is set in an appropriate range since the fusion-bonding strength of a heat-sealed portion is gradually lowered when a ratio of the width of the beam passage portion to the spot diameter of a laser beam 30 is set to be too large.

From these points of view, a ratio (W7/D) of the width W7 of the beam passage portion (the slit-like opening) to the spot diameter D of a laser beam 30 is preferably 1.2 or more, more preferably 1.4 or more, and preferably 20 or less, more preferably 10 or less.

The results illustrated in FIG. 8 are results that are obtained when the portion 10C, which is to be divided and which has a four-layer structure is irradiated with a laser beam, and results, which are obtained when the portion 10C, which is to be divided and which has an eight-layer structure is irradiated with a laser beam, are slightly different from the results illustrated in FIG. 8. However, it is also possible to form fusion-bonded portions, which include narrow sections, at the portion 10C, which is to be divided and which has an eight-layer structure even under the same conditions; and it is also possible to form the same fusion-bonded portions, which include the narrow sections, as the fusion-bonded portions of the portion 10C, which is to be divided and which has a four-layer structure at the portion 10C, which is to be divided and which has an eight-layer structure, by changing the width of a beam passage portion at a portion, which is to be irradiated with a laser beam, of the outer cover having a four-layer structure and the width of a beam passage portion at a portion, which is to be irradiated with a laser beam, of the outer cover having an eight-layer structure, as necessary.

Accordingly, it is also easy to form the side seal 4, in which the fusion-bonded portion 40 including the narrow section 4F and the broad sections 4A and 4B provided on both sides of the narrow section 4F is formed over the entire length of the portion between the waist opening 8 and the leg opening 9, in the diaper 1.

The cut edge portions of the sheets 31 and 32 generate heat and are melted during the irradiation of a laser beam 30 and immediately after the completion of the irradiation of a laser beam. However, while the pressurized state, which is made by the support member 21 and the pressurizing belt 24, of each of single sheet-shaped diaper precursor, which is separated from the continuous diaper 10 by the irradiation of a laser beam 30, and the continuous diaper 10 is maintained, the cut edge portions of the sheets 31 and 32 are promptly cooled and solidified by external air from the completion of irradiation and form a fusion-bonded portion 40 in which the materials (fibers or the like) of the cut edge portions are melted and integrated with each other. The fusion-bonded portion 40 is formed in this way, so that one of the pair of side seals 4 and 4 of single diaper 1 is formed. Meanwhile, the cut edge portions of the sheets 31 and 32 may be forcibly cooled by using known cooling means, such as a suction device or an exhaust device, as necessary, so that the formation of the fusion-bonded portion 40 is facilitated.

After one portion 10C to be divided (a portion where the side seals 4 are to be formed) is divided in this way, the irradiation point of a laser beam 30 is moved so as to be aimed at an another opening 27 adjacent to the opening 27 in a direction opposite to the transporting direction A and an another portion 10C, which is to be divided and which is positioned on the another opening 27, is irradiated with a laser beam through the another opening 27. Accordingly, the another portion 10C to be divided is divided and fusion-bonded in the same manner as described above, and an another side seal 4 (a fusion-bonded portion 40), which makes a pair with the side seal 4 having been previously formed, is formed. The same operation is repeated afterward, so that a pull-on disposable diaper 1 including the outer cover 3 having the pair of side seals 4 and 4 is continuously manufactured.

In the diaper 1 that is manufactured in this way, the seal edge portion 41, where the edge portions of the outer cover 3 in the front body portion F and the edge portions of the outer cover 3 in the back body portion R are bonded to each other by the continuous linear fusion-bonded portion 40 extending in the longitudinal direction of the side seal, is formed at the side seal 4.

Further, it is preferable that a portion of the continuous diaper 10 present in the vicinity of the portion 10C to be divided is irradiated with a laser beam while being pressurized, a laminate, in which fibers of cut ends are melted, is conveyed while the pressurized state of the laminate is maintained, and the pressurized state of the laminate is released after the solidification of a melted resin. The outer edge 4g of the fusion-bonded portion 40 of the seal edge portion 41, which is obtained in this way, has a shape that is dented so as to be convex toward the inside of the garment in the cross-section that is orthogonal to the direction in which the side seal 4 extends during wearing. In terms of the facilitation of the solidification of a melted resin, it is preferable that the continuous diaper is pressurized in a state that a member made of metal excellent in thermal conductivity comes into contact with at least one surface of the continuous diaper or it is preferable that the continuous diaper is cooled by air equipment or the like.

Meanwhile, as illustrated in FIG. 4, on a side outside of the fusion-bonded portion 40 in the inner-to-outer direction P, the seal edge portion 41 of the diaper 1, which is obtained from the above-mentioned manufacturing method, does not include a portion in which constituent fibers of the outer cover 3 retain their fibrous form. For this reason, when a wearer wears the diaper 1, the visibility of the fusion-bonded portion 40 can deteriorate. Accordingly, the appearance of the diaper 1 becomes similar to underwear.

The diaper 1 including the pair of side seals 4 and 4, which is obtained from the step in which the division and fusion-bonding of the outer cover 3 are simultaneously performed, is excellent in the flexibility and texture of the side seal 4, and the diaper 1 has good wearing comfort.

A laser beam will be described. A laser beam having a wavelength, which is absorbed by the sheets (the outer sheet 31 and the inner sheet 32) of the outer cover 3 and allows the sheets to generate heat, is used as a laser beam that irradiates the continuous diaper 10 (continuous outer cover 3). Here, "the sheet of the outer cover" is not limited to a sheet that forms one surface (the surface coming into contact with the support member 21) of the outer cover (for example, the outer sheet 31 in the above-mentioned aspect), and may be any sheet of the outer cover. Whether or not a laser beam irradiating the outer cover is a laser beam having a wavelength, which is absorbed by each sheet of the outer cover and allows the sheet to generate heat, is determined by a relationship between the material of the sheet and the wavelength of a laser beam to be used. When the sheet of the outer cover is a nonwoven fabric or a film that is made of a synthetic resin widely used to manufacture an absorbent article (sanitary article), such as a disposable diaper or a sanitary napkin, it is preferable that $CO_2$ laser, YAG laser, LD laser (semiconductor laser), YVO4 laser, fiber laser, or the like is used as a laser beam. Further, when the sheet of the outer cover contains polyethylene, polyethylene terephthalate, or polypropylene as a synthetic resin, a wavelength, which is absorbed by the sheet and allows the sheet to generate heat well, is preferably 8.0 µm to 15.0 µm and even more preferably 9.0 µm to 11.0 µm of the oscillation wavelength of $CO_2$ laser in which a high-output laser device is present. The spot diameter, the laser output, and the like of a laser beam can be appropriately selected in consideration of the material, the thickness, and the like of the sheet of the outer cover.

The invention has been described above on the basis of the embodiment thereof, but can be appropriately modified without being limited to the above-mentioned embodiment.

For example, the continuous outer cover (the sheet laminate) includes four disposed sheets as illustrated in FIG. 7(a), but may include two disposed sheets, three disposed sheets, or five or more disposed sheets. Furthermore, the laser type joining device 20 may be provided with a mechanism for controlling the tension of the continuous diaper 10 to wind the continuous diaper 10 on the cylindrical roller 23 (the support member 21) without causing wrinkles or the slack.

Moreover, as illustrated in FIG. 3, the outer cover 3 of the embodiment (aspect) has a continuous shape, such as the shape of an hourglass, extending over the front portion 1A, the crotch portion 1C, and the rear portion 1B without being divided into the front portion 1A and the rear portion 1B. However, the outer cover in the invention is limited to a continuous shape, and may be divided into a front sheet member that is worn about the wearer's belly side (front side) and a rear sheet member that is worn about the wearer's back side (rear side), and the absorbent assembly may be bridged over and fixed to both the front sheet member and the rear sheet member. In the superposing-pressurizing step of a method for manufacturing a pull-on disposable diaper including the division type outer cover, portions, where side seals are to be formed, of a continuous outer cover, which has a structure in which a front body portion side (a continuous front sheet member) and a back body portion side (a continuous rear sheet member) of the continuous outer cover to which the absorbent assemblies are fixed are superposed, are pressurized.

Further, in the embodiment, before the superposing-pressurizing step is performed, both the lateral side portions 3a and 3a of the continuous outer cover 3 along the transporting direction, that is, both lateral side portions of the continuous outer sheet 31 and the continuous inner sheet 32 along the transporting direction are folded so as to cover both the longitudinal ends of the absorbent assemblies 2 as illustrated in FIG. 5. However, a continuous outer sheet of which the length in the width direction (a direction orthogonal to the longitudinal direction) is longer than that of the continuous inner sheet 32 may be used as the continuous outer sheet 31, and only extension portions, which extend outward from the side edges of the inner sheet 32, of the outer sheet 31 may be folded so as cover both the longitudinal ends of the absorbent assemblies 2 when the continuous outer sheet 31 and the continuous inner sheet 32 are superposed. In this case, each of an end of the waist opening 8 of the portion 10C to be divided of the continuous diaper 10 and the vicinity thereof is formed of a six-layer structural portion in which six sheets are superposed, and each of other portions of the portion 10C to be divided is formed of a four-layer structural portion in which four sheets are superposed. Furthermore, both the lateral side portions 3a and 3a of the continuous outer cover 3 along the transporting direction, that is, both lateral side portions of the continuous outer sheet 31 and the continuous inner sheet 32 along the transporting direction may not be folded.

Moreover, in a method for manufacturing a pull-on garment, instead of adjusting a ratio of the width of the beam passage portion to the spot diameter of a laser beam to form the fusion-bonded portion including the narrow section and the broad sections in the side seal-forming step, a support member, which includes a protrusion protruding toward the outer cover and formed in the vicinity of the beam passage portions on the outer surface with which the outer cover comes into contact, may be used in the side seal-forming step and a fusion-bonded portion including a narrow section and broad sections may be formed through the adjustment of the height of the protrusion.

Figure 10A:
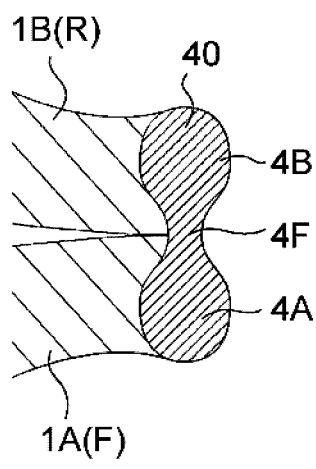
FIGS. 10(a) and 10(b) are cross-sectional views illustrating a cross-section that illustrates side seals of a diaper according to another embodiment of the invention and the vicinities of the side seals and is orthogonal to a direction in which the side seals extend.
Figure 10B:
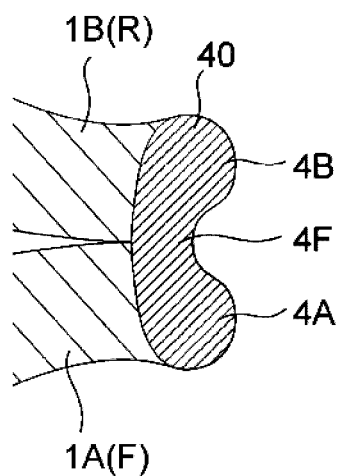

Further, the cross-sectional shape of the fusion-bonded portion 40 in the cross-section, which is orthogonal to the direction in which the side seal 4 extends, may be a shape illustrated in FIG. 10(a) or 10(b).

Furthermore, the pull-on garment of the invention is not limited to a pull-on disposable diaper, and may be a pull-on sanitary napkin and may be a diaper cover that includes an outer cover forming the outer surface of the garment and does not include an absorbent assembly.

Portions, of which the description is omitted, of the above-mentioned embodiment and components, which are included in only one embodiment, can be appropriately applied to other embodiments, and the components of each embodiment can be appropriately substituted between the embodiments.

The following additional remarks (the pull-on garment and the method for manufacturing pull-on garment) will be further disclosed in regard to the above-mentioned embodiment (aspect) of the invention.

<1>

A pull-on garment that includes an outer cover forming an outer surface of the garment, both lateral side edge portions of the outer cover in a front body portion and both lateral side edge portions of the outer cover in a back body portion being joined to each other to form a pair of side seals, a waist opening, and a pair of leg openings, wherein each of the side seals includes a seal edge portion where the edge portion of the outer cover in the front body portion and the edge portion of the outer cover in the back body portion are bonded to each other by a continuous linear fusion-bonded portion extending in a longitudinal direction of the side seal, in a cross-section orthogonal to a direction in which the side seal extends, when a direction directed from a side closer to the skin of a wearer toward a side farther from the skin of the wearer of the garment is referred to as an inner-to-outer direction and a direction orthogonal to the inner-to-outer direction is referred to as a thickness direction, the fusion-bonded portion includes a narrow section which is formed at a middle portion thereof in the thickness direction and of which a width along the inner-to-outer direction is small, and the narrow section is a section where broad sections are located on both sides of the narrow section in the thickness direction, and the width of the broad section is larger than the width of the narrow section.

<2>

The pull-on garment as set forth in clause <1>, wherein, in the thickness direction of the fusion-bonded portion, the narrow section is formed at a portion of the fusion-bonded portion where a boundary of the outer covers is present.

<3>

The pull-on garment as set forth in clause <1> or <2>, wherein, in the cross-section orthogonal to the direction in which the side seal extends, an outer edge of the fusion-bonded portion in the inner-to-outer direction has a cross-sectional shape that is dented so as to be convex toward the inside in the inner-to-outer direction.

<4>

The pull-on garment as set forth in any one of clauses <1> to <3>, wherein, in the cross-section orthogonal to the direction in which the side seal extends, an inner edge of the fusion-bonded portion in the inner-to-outer direction has a cross-sectional shape that protrudes so as to be convex toward the inside in the inner-to-outer direction.

<5>

The pull-on garment as set forth in any one of clauses <1> to <4>, wherein the fusion-bonded portion has a crescent cross-sectional shape as a whole in the cross-section orthogonal to the direction in which the side seal extends.

<6>

The pull-on garment as set forth in any one of clauses <1> to <5>, wherein the outer cover includes a resin material, and is made of the resin material serving as a main component.

<7>

The pull-on garment as set forth in any one of clauses <1> to <6>, wherein the outer cover contains a thermally fusible synthetic resin, such as polyethylene, polyethylene terephthalate, or polypropylene, as a resin material.

<8>

The pull-on garment as set forth in any one of clauses <1> to <7>, wherein the outer cover includes an outer sheet and an inner sheet which are made of a nonwoven fabric, and the nonwoven fabric is formed of an air-through nonwoven fabric, a heat-rolled nonwoven fabric, a spunlace nonwoven fabric, a spunbond nonwoven fabric, a meltblown nonwoven fabric, or a layered body in which one or two or more of these fabrics are layered so as to form two or more layers.

<9>

The pull-on garment as set forth in any one of clauses <1> to <8>, wherein, on a side outside of the fusion-bonded portion in the inner-to-outer direction, the seal edge portion does not include a portion in which constituent fibers of the outer cover retain their fibrous form.

<10>
The pull-on garment as set forth in any one of clauses <1> to <9>,
wherein the fusion-bonded portion, which includes the narrow section and the broad sections, is formed over the entire length of a portion between the waist opening and the leg opening.
<11>
The pull-on garment as set forth in any one of clauses <1> to <10>,
wherein the minimum width Wc of the narrow section of the fusion-bonded portion is preferably 95% or less, more preferably 90% or less of the maximum widths Wa and Wb of the broad sections provided on both sides of the narrow section, and preferably 20% or more, more preferably 30% or more of the maximum widths Wa and Wb of the broad sections provided on both sides of the narrow section, and preferably 20% to 95%, more preferably 30% to 90% of the maximum widths Wa and Wb of the broad sections provided on both sides of the narrow section.
<12>
The pull-on garment as set forth in any one of clauses <1> to <11>,
wherein the minimum width Wc of the narrow section of the fusion-bonded portion is preferably 3 mm or less and more preferably 2 mm or less.
<13>
The pull-on garment as set forth in any one of clauses <1> to <12>,
wherein the entire width Wd of the fusion-bonded portion in the inner-to-outer direction P is preferably 95% or less, more preferably 50% or less of the entire thickness td of the fusion-bonded portion, and preferably 10% or more, more preferably 30% or more of the entire thickness td of the fusion-bonded portion, and preferably 10% to 95%, more preferably 30% to 50% of the entire thickness td of the fusion-bonded portion.
<14>
The pull-on garment as set forth in any one of clauses <1> to <13>,
wherein the entire width Wd of the fusion-bonded portion in the inner-to-outer direction P is preferably 3 mm or less and more preferably 2 mm or less.
<15> The pull-on garment as set forth in any one of clauses <1> to <14>,
wherein the pull-on garment is a pull-on disposable diaper, and
the outer cover is positioned on a non-skin-facing surface side of an absorbent assembly including an absorbent member and fixes the absorbent assembly.
<16>
The pull-on garment as set forth in any one of clauses <1> to <15>,
wherein the outer cover includes an outer sheet that forms a non-skin-facing surface of the outer cover, an inner sheet that is disposed on an inner surface side of the outer sheet and forms a skin-facing surface of the outer cover, and a plurality of thread-shaped or belt-shaped elastic members that are fixed between the outer sheet 31 and the inner sheet by an adhesive.
<17>
A method for manufacturing the pull-on garment as set forth in any one of clauses <1> to <16>, the method including:
a superposing-pressurizing step of pressurizing a portion, of a continuous outer cover, where a side seal is to be formed in the state that the front body portion side and the back body portion side are superposed; and
a side seal-forming step of dividing the outer cover by irradiating the portion, where a side seal is to be formed and which is in the pressurized state, with a laser beam through a beam passage portion, which extends in a direction intersecting a transporting direction of the outer cover, and thereby cutting and separating the outer cover and fusion-bonding the layered outer cover's cut-edge portions that have been formed by the cutting/separation, wherein,
in the side seal-forming step, a support member where a ratio of the width of the beam passage portion to the spot diameter of the laser beam is adjusted so that the fusion-bonded portion including the narrow section and the broad section is formed is used.
<18>
The method for manufacturing the pull-on garment as set forth in clause <17>,
wherein, in the side seal-forming step, the laser beam is irradiated by a laser type joining device, so that a side seal serving as the side seal of the pull-on garment is formed at each of the portions, where the side seals are to be formed, of the continuous outer cover in which the front body portion side and the back body portion side are superposed.
<19>
The method for manufacturing the pull-on garment as set forth in clause <18>,
wherein two side seals serving as the side seals of two pull-on garments are formed at each of the portions, where the side seals are to be formed, of the continuous outer cover in which the front body portion side and the back body portion side are superposed.
<20>
The method for manufacturing the pull-on garment as set forth in any one of clauses <17> to <19>,
wherein the laser type joining device includes: an irradiation head which emits a laser beam toward the support member; and a pressing member, and
pressure is applied to the continuous outer cover, in which the front body portion side and the back body portion side are superposed, by the support member and the pressing member.
<21>
The method for manufacturing the pull-on garment as set forth in any one of clauses <17> to <20>,
wherein the support member includes, as the beam passage portion through which a laser beam passes, a slit-like opening that penetrates the support member in a thickness direction.
<22>
The method for manufacturing the pull-on garment as set forth in any one of clauses <17> to <21>,
wherein the laser beam is applied in such a manner that the width W7 of the slit-like opening is set to be large relative to the spot diameter D of the laser beam.
<23>
The method for manufacturing a pull-on garment as set forth in any one of clauses <17> to <22>,
wherein a ratio (W7/D) of the width W7 of the beam passage portion (the slit-like opening) to the spot diameter D of the laser beam is preferably 1.2 or more, more preferably 1.4 or more, and preferably 20 or less, more preferably 10 or less.
<24>
The method for manufacturing the pull-on garment as set forth in clause <23>,
wherein the ratio (W7/D) is in the range of 5 to 7.

INDUSTRIAL APPLICABILITY

A pull-on garment of the invention is excellent in appearance, includes side seals excellent in flexibility or texture, and hardly causes lateral tears when the side seals are torn.

The invention claimed is:

1. A pull-on garment that includes an outer cover forming an outer surface of the garment, both lateral side edge portions of the outer cover in a front body portion and both lateral side edge portions of the outer cover in a back body portion being joined to each other to form a pair of side seals, a waist opening, and a pair of leg openings, wherein each of the side seals includes a seal edge portion where the edge portion of the outer cover in the front body portion and the edge portion of the outer cover in the back body portion are bonded to each other in a side-by-side configuration by a continuous linear fusion-bonded portion extending in a longitudinal direction of the side seal, in a cross-section orthogonal to a direction in which the side seal extends, when a direction directed from a side closer to the skin of a wearer toward a side farther from the skin of the wearer of the garment is referred to as an inner-to-outer direction and a direction orthogonal to the inner-to-outer direction is referred to as a thickness direction, the fusion-bonded portion includes a narrow section which is formed at a middle portion thereof in the thickness direction and of which a width along the inner-to-outer direction is small, and the narrow section is a section where broad sections are located on both sides of the narrow section in the thickness direction, and the width of the broad sections, respectively, along the inner-to-outer direction is larger than the width of the narrow section.

2. The pull-on garment according to claim 1, wherein, in the thickness direction of the fusion-bonded portion, the narrow section is formed at a portion of the fusion-bonded portion where a boundary of the outer covers is present.

3. The pull-on garment according to claim 1, wherein, in the cross-section orthogonal to the direction in which the side seal extends, an outer edge of the fusion-bonded portion in the inner-to-outer direction has a cross-sectional shape that is dented so as to be convex toward the inside in the inner-to-outer direction.

4. The pull-on garment according to claim 1, wherein, in the cross-section orthogonal to the direction in which the side seal extends, an inner edge of the fusion-bonded portion in the inner-to-outer direction has a cross-sectional shape that protrudes so as to be convex toward the inside in the inner-to-outer direction.

5. The pull-on garment according to claim 1, wherein the fusion-bonded portion has a crescent cross-sectional shape as a whole in the cross-section orthogonal to the direction in which the side seal extends.

6. The pull-on garment according to claim 1, wherein the outer cover includes a resin material, and is made of the resin material serving as a main component.

7. The pull-on garment according to claim 1, wherein the outer cover includes a resin material, and the resin material is a thermally fusible synthetic resin.

8. The pull-on garment according to claim 1, wherein, on a side outside of the fusion-bonded portion in the inner-to-outer direction, the seal edge portion does not include a portion in which constituent fibers of the outer cover retain their fibrous form.

9. The pull-on garment according to claim 1, wherein the fusion-bonded portion, which includes the narrow section and the broad sections, is formed over the entire length of a portion between the waist opening and the leg opening.

10. The pull-on garment according to claim 1, wherein the minimum width We of the narrow section of the fusion-bonded portion is 95% or less of the maximum widths Wa and Wb of the broad sections provided on both sides of the narrow section.

11. A method for manufacturing the pull-on garment according to claim 1, the method comprising:

a superposing-pressurizing step of pressurizing a portion, of a continuous outer cover, where a side seal is to be formed in the state that the front body portion side and the back body portion side are superposed; and a side seal-forming step of dividing the outer cover by irradiating the portion, where a side seal is to be formed and which is in the pressurized state, with a laser beam through a beam passage portion, which extends in a direction intersecting a transporting direction of the outer cover, and thereby cutting and separating the outer cover and fusion-bonding the layered outer cover's cut-edge portions that have been formed by the cutting/separation, wherein, in the side seal-forming step, a support member is used where a ratio of the width of the beam passage portion to the spot diameter of the laser beam is adjusted so that the fusion-bonded portion including the narrow section and the broad sections is formed.

12. The method for manufacturing the pull-on garment according to claim 11, wherein the support includes, as the beam passage portion through which a laser beam passes, a slit-like opening that penetrates the support in a thickness direction.

13. The method for manufacturing the pull-on garment according to claim 11, wherein the laser beam is applied in such a manner that the width W7 of the beam passage portion is set to be large relative to the spot diameter of the laser beam.

14. The method for manufacturing the pull-on garment according to claim 11, wherein a ratio (W7/D) of the width W7 of the beam passage portion to the spot diameter of the laser beam is 1.2 or more.

15. The method for manufacturing the pull-on garment according to claim 14, wherein the ratio (W7/D) is in the range of 5 to 7.

* * * * *